United States Patent
Chevillon et al.

[11] Patent Number: 5,968,071
[45] Date of Patent: Oct. 19, 1999

[54] BLOOD FILTERING DEVICE HAVING IMPROVED PERMEABILITY

[75] Inventors: Gérard Chevillon, Montrouge; Guy Nadal, Poitiers, both of France

[73] Assignee: B. Braun Celsa, France

[21] Appl. No.: 08/996,294

[22] Filed: Dec. 22, 1997

[30] Foreign Application Priority Data

Jan. 3, 1997 [FR] France .................................... 97 00032

[51] Int. Cl.[6] .................................................. A61M 29/00
[52] U.S. Cl. .......................................................... 606/200
[58] Field of Search ................................... 600/200, 198, 600/169, 191, 199

[56] References Cited

U.S. PATENT DOCUMENTS

| | | | |
|---|---|---|---|
| 4,727,873 | 3/1988 | Mobin-Uddin | 128/303 |
| 4,817,600 | 4/1989 | Herms et al. | 128/303 |
| 4,969,891 | 11/1990 | Gewertz . | |
| 5,059,205 | 10/1991 | El-Nounou et al. . | |
| 5,133,733 | 7/1992 | Rasmussen et al. . | |
| 5,300,086 | 4/1994 | Gory et al. . | |
| 5,324,304 | 6/1994 | Rasmussen . | |
| 5,344,427 | 9/1994 | Cottenceau et al. . | |
| 5,634,942 | 6/1997 | Chevillon et al. | 623/1 |
| 5,725,550 | 3/1998 | Nadal | 606/200 |

FOREIGN PATENT DOCUMENTS

| | | |
|---|---|---|
| 0582493 | 2/1994 | European Pat. Off. . |
| 0655228 | 5/1995 | European Pat. Off. . |
| 2718950 | 10/1995 | France . |
| 2713081 | 1/1996 | France . |
| 96 17634 | 6/1996 | WIPO . |

Primary Examiner—Michael Buiz
Assistant Examiner—Tina T. D. Pham
Attorney, Agent, or Firm—Rothwell, Figg, Ernst & Kurz

[57] ABSTRACT

The invention relates to a blood filter that is to be positioned within a blood vessel to trap blood clots. The filter includes a head to which there are attached and from which there extend several legs comprising at least one elongated element having two opposite ends. The legs are radially movable and the elongated element of at least some of these legs has a shape folded back upon itself, substantially in the form of a loop. According to the invention, one of the ends of at least some of these elongated elements is disposed at a distance from the inside of the head of the filter.

8 Claims, 3 Drawing Sheets

FIG_1
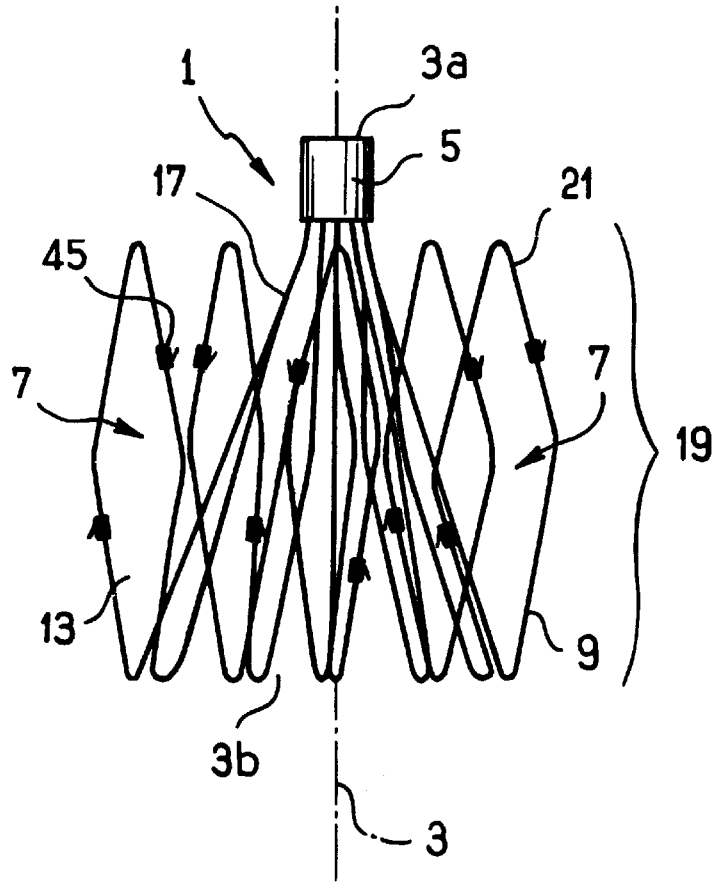
FIG_2
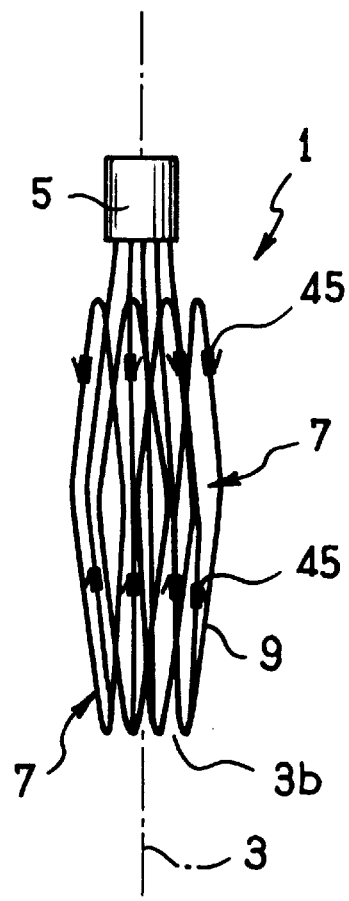
FIG_3
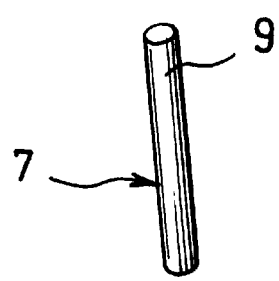
FIG_4
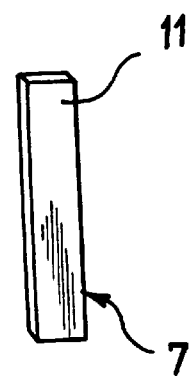

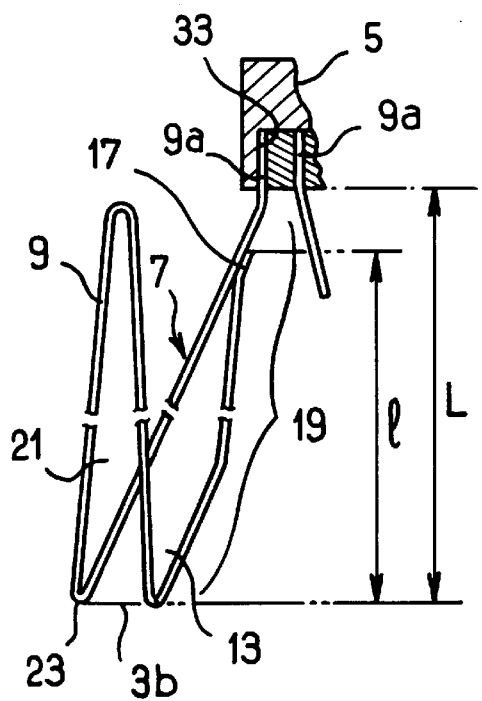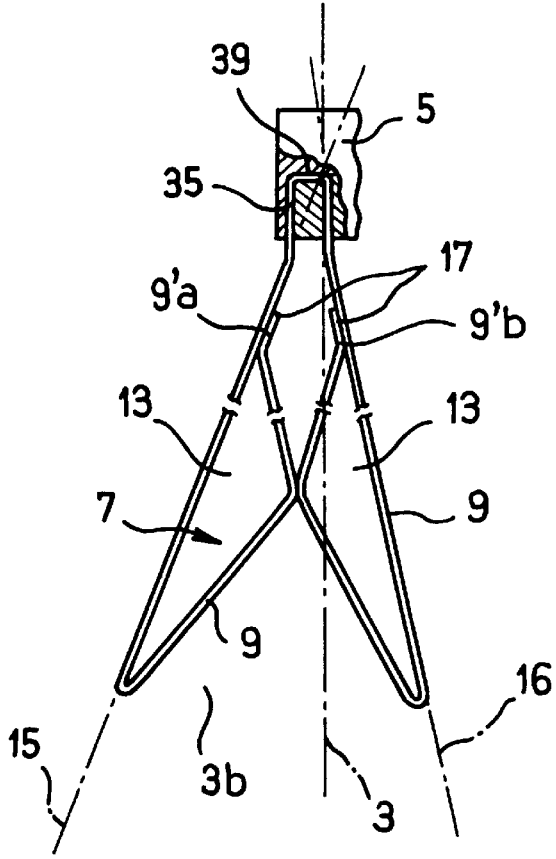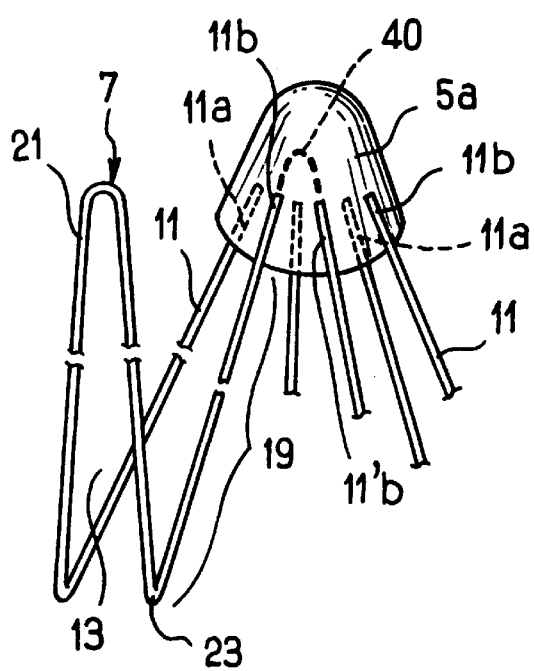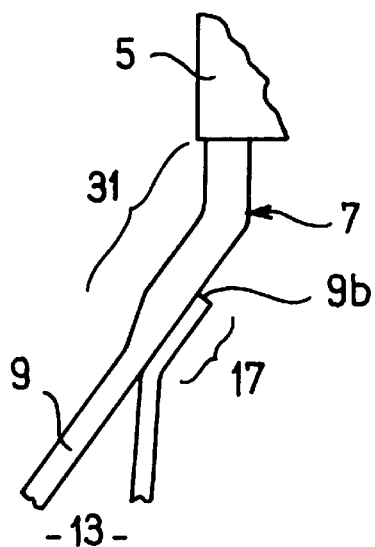

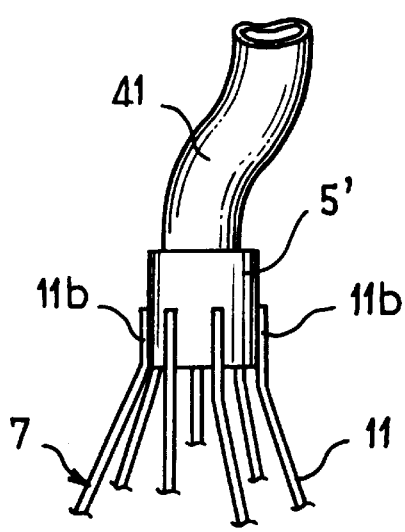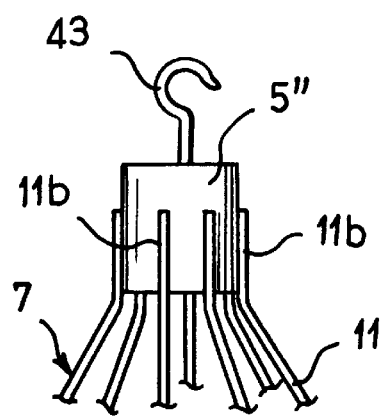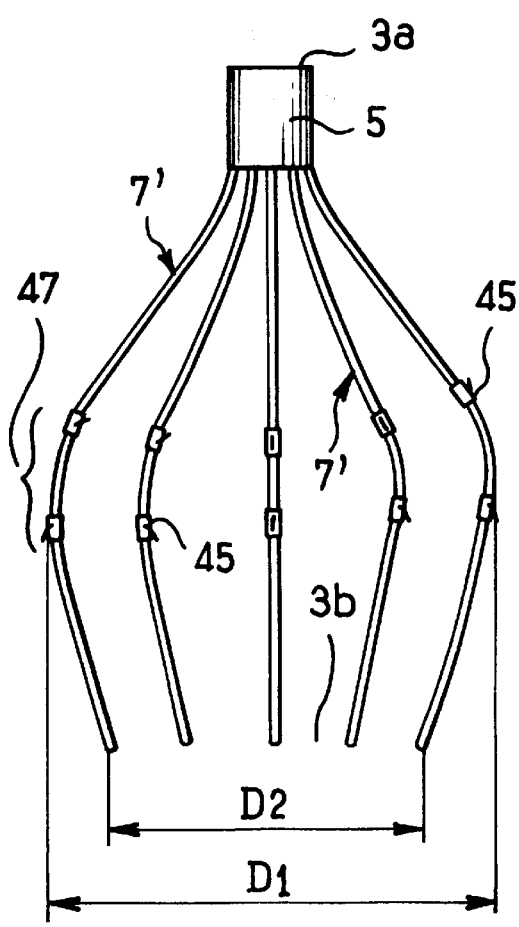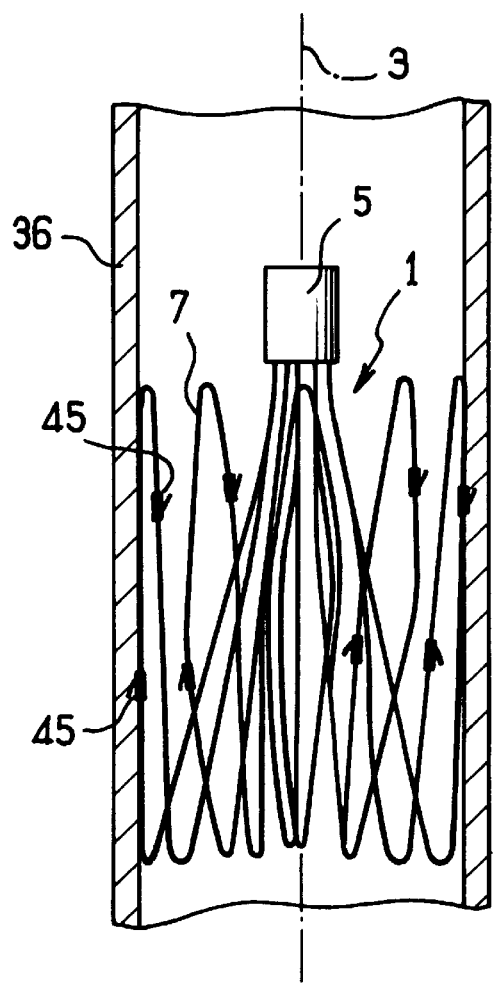

BLOOD FILTERING DEVICE HAVING IMPROVED PERMEABILITY

BACKGROUND OF THE INVENTION

The invention relates to a blood filter that is to be positioned within a blood vessel to trap blood clots carried along by the flow of blood. It should be noted at this point that the filter according to the invention can be both a "definitive" (or permanent) filter and a "temporary" filter, that is a filter which can be implanted in a vessel and which can be left there permanently, or removed after a given period of implantation (nowadays typically of the order of a fortnight).

Conventionally, a filter known as a "definitive" implantation filter is provided with means for fastening or attachment to the wall of the vessel in which it is implanted.

Some examples of such filters are described in U.S. Pat. No. 5,059,205, U.S. Pat. No. 5,133,733 or U.S. Pat. No. 5,344,427. However, some such blood filters are also known which have hooks for attachment to the wall of the vessel and which are nevertheless defined as being removable or repositionable, as long as the period for which they have been positioned in a specific location within a vessel has not been too long and cellular development does not in practice prevent them from being moved. U.S. Pat. No. 5,324,304 describes such a filter whose head has a hook enabling the filter to be caught.

However, other filters defined as "temporary", that is removable under the conditions outlined above, are such that the filter itself is attached to a long, flexible carrier tube (often a catheter) which meanders through the body of the patient as far as the cutaneous surface region from which the filter was introduced into the vascular system, this elongate tube even generally protruding outside the patient's body. Some examples of such filters are described in U.S. Pat. No. 5,300,086, in FR-A-2 713 081 or in U.S. Pat. No. 4,969,891.

Among these different types of filter, the one according to the invention is, structurally, more especially a filter having an axis and comprising a head which is arranged substantially on that axis and to which there are attached and from which there extend several legs or limbs, comprising at least one elongate (filiform) element having a first end and a second, opposite end, the legs being radially movable between a radially expanded state and a radially contracted state in which the legs are brought close to the axis, the elongate element of at least some of these legs being in a form folded back upon itself, substantially in the form of a loop.

A filter with such a structure is disclosed in U.S. Pat. No. 5,344,427.

However, that filter, like those mentioned above, still has defects in regard to the permeability of its head in respect of blood circulation.

This is a critical problem since the filter must be capable of trapping and retaining blood clots of at least a given size, but it must not excessively disrupt the blood circulation or the vessel in which it is implanted.

These two constraints are difficult to satisfy simultaneously.

The filter's mechanical resistance, its suitability for implantation from a tube (catheter) having a small diameter and its reliability must also be taken into consideration.

SUMMARY OF THE INVENTION

The invention solves the problem by arranging, on a filter of the type described in U.S. Pat. No. 5,133,733 or FR-A-2 713 081 (pages 4 to 8), at least one of the ends of the elongate element(s) forming the legs at a distance from the inside of the head of the filter. In this manner, it is to be possible to bring nearer together the portions of the elongate elements attached to the filter head, whilst reducing the dimensions (especially the radial dimensions) of that head, which measure is to improve the permeability of the filter head in respect of blood circulation.

This solution can also be applied to a blood filter having other structural features, such as the filter disclosed in U.S. Pat. No. 5,344,427. The filter described in that patent is a blood filter in the case of which, in addition to the above-mentioned features, the legs, each comprising an elongate (filiform) element, have a length dependent on their elongation, in their expanded state, these legs are, over part of their length, inclined relative to the filter axis so that they together define an axial corolla, the first end of the elongate elements forming the legs is attached to the inside of the head of the filter, and, especially, the form folded back on itself, substantially in the form of a loop, of at least some of the elongate elements is, also bent substantially in the shape of a hairpin, such that the legs concerned have, around the corolla, a centring foot substantially parallel to the filter axis, following their inclined portion.

On reading U.S. Pat. No. 5,344,427 (which is included in this description by reference, as are the other patents mentioned), the importance of these centring feet (known as "hairpins" or "pins") will be noted. It will also be noted, especially when looking at FIGS. 4, 5 and 15, that the two opposite ends of each of the elongate elements forming the legs are to be attached to the inside of the filter head which means, of course, that the head must be dimensioned accordingly.

In contrast, according to the invention, it is recommended that one of the ends of at least some of these elongate elements be arranged at a distance from the inside of the head of the filter.

A consequent problem which is solved by the invention concerns the manner in which this elongate element end, located at a distance from the inside of the head of the filter, is to be arranged. It has already been stated above that the filter must have adequate filtration capacity without, however, being too cumbersome or too disruptive, whilst remaining mechanically resistant.

Therefore, a complementary feature of the invention provides that the second end of an elongate leg element should be attached to the elongate element itself in order to close the loop.

The legs concerned will, therefore, be attached to the head of the filter only by a single portion of the elongate element, whilst they are attached by two portions, notably in U.S. Pat. No. 5,344,427 or FR-A-2 713 081. Despite this, it might be thought that this connection by means of a single strand between the legs and the head will excessively weaken the mechanical strength of the legs and/or their radial resistance to the reaction of the walls of the vessel when the filter is implanted.

Therefore, a complementary feature of the invention provides for the possibility that this second end of the elongate element(s) will nevertheless be attached to the head of the filter, but in that case to the outside of the head.

It would thus be possible to attach half of the elongate elements (metal wires, for example) to the inside of the head and the other half to the outside of the head.

The advantage of this solution over the previous solution is that it would not weaken the assembly of the legs at the filter head, whilst increasing the distance separating two consecutive strands.

However, if the first solution of attaching the second end of a particular elongate element to itself to close the loop is taken up again, it will be evident that there is an advantage in locating this attachment of the element to itself on the portion of the legs which expands to form the corolla, this being effected on a filter having a centring foot of the type described in U.S. Pat. No. 5,344,427.

It will therefore be possible to benefit from the filtration capacity of two strands of wire, instead of one, not only where the foot is located, but also at the corolla portion.

In this connection and, once more, to promote the mechanical strength of the filter, another feature of the invention indicates that it is advantageous to arrange this attachment of the elongate element to itself nearer to the head of the filter than to the centring foot of the leg concerned.

Additionally or alternatively to this, it may also prove necessary to increase the section of the elongate element (for example, to increase the diameter of the round wire(s) forming the legs) near to the head of the filter and/or on the portion of the elongate element located outside the loop, that is, therefore, on the portion where the leg concerned has only a "single" structure, to be distinguished from the "double" structure where the loop is arranged.

BRIEF DESCRIPTION OF THE DRAWINGS

There now follows a more detailed description of the invention which refers to the appended drawings, in which:

FIG. 1 is a diagrammatic front view of the filter according to the invention with its legs depicted in their radially expanded position;

FIG. 2 shows the filter of FIG. 1, with its legs in the radially contracted position;

FIG. 3 shows one possible embodiment of a portion of the elongate element forming the legs;

FIG. 4 shows a variant of the portion of FIG. 3;

FIG. 5 shows one of the legs of the filter of FIG. 1, including its attachment to the head;

FIG. 6 shows a partial diagrammatic view of a variant for attaching the legs to the filter head;

FIG. 7 also shows (partially cut away as in FIG. 5) another manner of producing the filter's legs and of attaching them to the head;

FIG. 8 is an enlarged view of a detail of FIG. 5;

FIG. 9 shows a portion of the filter, for providing a temporary filter;

FIG. 10 also shows a portion of the filter, for providing a repositionable (even removable) filter;

FIG. 11 shows the filter of FIG. 1, assumed to be in the expanded position inside a blood vessel;

and FIG. 12 shows an external front view of another variant of a filter according to the invention.

Firstly, FIG. 1 shows a blood filter 1 according to the invention which is to trap and retain blood clots of a size equal to or greater than 5 mm or 6 mm (within±10%).

DETAILED DESCRIPTION OF PREFERRED EMBODIMENTS

The filter has a general axis 3, a proximal axial end 3a and a distal axial end 3b.

The filter comprises a head 5 at its proximal end, substantially on the axis 3. A series of flexible, elongate legs 7, for example a quantity of four, are attached to the head, distributed in an angular and substantially regular manner around the axis 3, so that the legs expand resiliently, firstly substantially in the form of a conical, axial corolla starting from the head, into their radially expanded position according to FIG. 1.

This will typically be the legs non-constrained position of rest. FIG. 2 shows that these same legs 7 can also occupy a radially contracted position in which they are brought close to the axis 3, relative to which they extend substantially parallel here.

This can typically be the radially constrained position of the legs which they will be caused to adopt especially in order to position the filter inside the vessel, as is known (if necessary, refer to the aforementioned patents, and especially U.S. Pat. No. 5,344,427 or U.S. Pat. No. 5,324,304).

As diagrammatically illustrated in FIG. 3, all or some of the legs 7 can be produced from a round or substantially round (oval, ovoid, . . . ) wire 9, such as, especially, a metal wire of stainless steel (for example, with the reference AFNOR K13 C20 N16 Ne15, marketed under the brand name "PHYNOX", the wire having a diameter of from 2 to 4 tenths of a millimeter, approximately). The same metal can be used for the head.

As illustrated in FIG. 4, the legs 7 could also be produced from a fine metal plate (for example, the same material as above) 11, even if, a priori, the use of a round wire is preferable.

A plastics material can also be used in place of the metal, the material selected in any case being biocompatible.

Referring once more to FIG. 1, but equally to FIGS. 5, 6 and 7, it will be noted that all or some of the legs 7 are in the form of a loop, achieved by folding the elongate elements 9 or 11 back upon themselves.

In FIG. 7 the loops 13 are of an ovoid shape or are more or less in the form of an elongate trapezium, each leg, in its radially expanded state, extending in a direction (such as 15, 16) inclined relative to the axis 3, whilst being concurrent relative to one another and relative to the axis 3, at the proximal end 3a.

In FIGS. 1, 2, 5 and 7, the loop formed by one of the folded wires 9 is a closed loop. An enlarged view of this "closure" can be seen in FIG. 8. It can thus be observed that the end 9b of a particular wire 9 is, at a distance from the head, attached to the wire itself (for example, by welding, adhesive bonding, . . . ) after the wire has been folded into the shape of a loop to form the closed space 13.

Advantageously, the zone 17 where the wire is attached to itself will be located between the distal end 3b and the head 5, that is on the part of the legs forming the corolla, in the radially expanded position of the filter.

It is even advisable, as clearly shown in FIGS. 1, 5 and 7, that this zone 17 be located nearer to the head 5 than to the distal end 3b. Thus, FIG. 5 shows that, if an axial distance L separates the head 5 from the end 3b, the axial distance I between said distal end 3b and the zone 17 may be approximately from two thirds to four fifths of the length L.

Moreover, FIG. 7 clearly shows that the legs 7 extend substantially in a rectilinear or, optionally, a slightly curved direction with a concavity towards the axis 3 (directions 15 and 16). On the other hand, FIGS. 1, 5 and 6 show that the legs 7 are extended by what would be termed a "centring foot" 21 beyond and around their portion 19 which is in the form of a corolla.

In comparison with FIG. 7, each foot 21 therefore extends the relevant legs of the filter beyond the distal end 3b, but without necessarily extending the axial length L of the legs, since the feet 21 return towards the head 5 (in this case common to all the legs), the two strands of the elongate elements 9 or 11 forming the legs each being, for this purpose, folded more or less into a hairpin shape, at 23.

With these feet 21, the loop 13 is therefore folded substantially into a "V" shape (in the filter's radially expanded state). Reference should be made to U.S. Pat. No. 5,344,427 (columns 3 and 4) for further details.

Be that as it may, with such a loop 13 closed at 17, the attachment of the concerned legs to the head 5 can be performed individually only by means of a single strand of elongate element 9 or 11.

As a result, the diameter or the cross-section of the leg portion located between the closure zone 17 of the loop 13 and the zone of attachment to the head 5 (portion marked 31 in FIG. 8) can be increased.

As regards the attachment of the IEGs to the common head 5, this can be performed especially by one of the methods disclosed in U.S. Pat. No. 5,344,427.

Briefly, it is firstly possible to attach the end 9a of each elongate element concerned (opposite the aforementioned end 9b) to the inside of the head in a passage 33 parallel to the axis 3, as illustrated in FIG. 5.

Therefore, a series of passages 33 can be distributed around this axis inside the head of the filter to receive each of the legs 7, the leg being tightly engaged in the corresponding space 33 where it is then fixed (preferably welded or adhesively bonded). By way of variation, as illustrated in FIG. 7, there is also the possibility of using an elongate element, such as a metal wire 9, longer than that in FIG. 5, and of inserting a substantially central portion 39 of the wire inside a "U"-shaped passage 35 in the head 5, the two free ends 9'a, 9'b of the wire then each being attached, at 17, to the wire itself to form the desired loops.

Optionally, the end 9'b of the wire could even be extended in order to be inserted once or several times more inside the head and thus to develop the legs around the entire periphery of the head, starting from a single wire, with a series of "U"-shaped passages 35 optionally meeting inside the head.

FIGS. 6, 9 and 10 illustrate another method of folding the legs in two and attaching them to the filter head.

In this particular case, as shown more clearly in FIG. 6, the two opposite ends 11a, 11b of the same elongate element 11 are brought up to the head 5, where they are attached respectively to the inside and outside of the head, after the looped leg 7 has been defined, optionally with its foot 21.

The end 11a can be attached to the inside of the head as in FIG. 5, in a passage parallel to the axis 3.

On the exterior, the opposite end portion 11b of the same element is placed against the surface 5a of the head, to which this end portion is attached by any appropriate means, such as welding or adhesive bonding. As a result, the loop formed will not be completely closed, because the thickness of the head separates the two ends 11a, 11b, which can, however, be brought closer together to a greater or lesser extent, and even overlap.

It should be noted that, even if an element 11 is extended by a portion (indicated by broken line 40 in FIG. 6) in order to connect to one another two successive ends (such as 11b and 11'b) of two adjacent elements 11 attached to the head, this would still be considered an attachment to the head of the filter by one "end" of the elongate element. The same consideration can be applied to FIG. 7, in respect of the wire portion 39.

In FIGS. 9 and 10, the attachment of the legs is the same as in FIG. 6.

However, these two Figures are principally of interest in respect of the complementary means with which their head (5' and 5" respectively) is provided, in order to permit or facilitate the movement of the filter inside the vessel which is to receive it, and even the removal of the filter after a given period of implantation.

Thus, in FIG. 9, the filter head is attached, opposite the legs, to a catheter or a flexible rod 41, typically used for handling temporary filters, as 10 disclosed notably in FR-A-2 713 081 or U.S. Pat. No. 5,300,086, the flexibility of the tube 41 being such that it can pass without sustaining damage into the vascular access path, from outside the patient's body as far as the vessel 36 receiving the filter (see FIG. 11).

In FIG. 10, the head 5" has a hook 43 instead of the tube 41, as provided for in U.S. Pat. No. 5,324,304 (means called a retrieval hook), the hook 43, of course, being for use in combination with the complementary means described in this patent.

As a result, the filter according to the invention can be a temporary filter, or at least a filter which can be moved inside the vessel which receives it.

If, after all, it is a "definitive" filter, it will advantageously be provided (conventionally) with means of attachment to the wall of the vessel. For this purpose, the walls of the legs could be chemically treated to promote locally their adhesion to that wall.

As a complementary or alternative solution, hooks can be provided on the legs, as illustrated in FIGS. 1, 2 and 12.

These hooks, marked 45, can be set alternately in the direction towards the proximal end 3a and the distal end 3b, in order to ensure that the filter is held securely in both directions, substantially on the axis 3.

The hooks 45 can be produced and attached in the manner disclosed in U.S. Pat. No. 5,344,427.

These hooks have been arranged on the elongate elements forming the legs of the filter and, more accurately, in the area of a portion coming closely into contact with the wall of the vessel in the filter's radially expanded state.

As a result, these hooks are found in the area of the feet 21, as in FIGS. 1 and 2, and on the most bulging portion (therefore having the greatest diameter) 47 as in FIG. 12.

In this Figure, it will be noted how the legs 7' curve outwards in the filter's radially expanded position, and therefore have an internal concavity. It should be noted that the legs 7' can be produced from wire (9) or narrow plate (11), and with or without a loop.

In this particular case, the legs are in the form of metal wires slightly curved in an arc shape, the legs of the filter in the radially expanded position having an intermediate diameter, D1, which is greater than the distal diameter D2, when opened, of those legs at 3b, which diameter is itself greater than the diameter D1 of the legs at the proximal end 3a, at the point where the legs are attached to the head 5, in this particular case in the manner represented in FIG. 6, that is some inside and others outside the head 5, with alternation of every other leg in this case.

However, it will be appreciated that the legs 7' could be double legs and could correspond especially to those in FIG. 5, 6 or 7.

It should be noted that this form of the legs shaped in an outwardly curved "arc" must intrinsically enhance the permeability of the filter head. The positive effect is reinforced by the fact that the smaller the diameter of the implantation vessel (vena cava), the more the cone will be urged to open at the top, which is counter to the fact that a filter is generally all the more "thrombogenic" if it is located in a vessel having a small diameter.

What is claimed is:

1. A blood filter adapted to be disposed in a blood vessel for retaining blood clots, the blood filter having an axis and comprising:

a head disposed substantially on the axis, and a plurality of legs extending from the head, each of at least some of the legs of the plurality of legs comprising an elongated, filiform element having first and second ends, with the first end being connected to an inside portion of the head and the second end being looped back and connected to an intermediate portion of the leg to form a filiform leg loop, wherein the plurality of legs are movable between a radially expanded state and a radially restrained state.

2. A blood filter adapted to be disposed in a blood vessel for retaining blood clots, the blood filter comprising:

a head disposed substantially on an axis, and a plurality of legs extending from the head, each of at least some of the legs the plurality of legs comprising an elongated, filiform element having a first and a second end, with the first end connected to an inside portion of the head and the second end of the leg looped back to form a filiform leg loop and disposed within the vicinity of the first end but not inside the head, the filiform leg loop having a first portion extending away from the head at an angle with respect to the axis to form a corolla and having a second portion folded back toward the head to form an angle with respect to the first portion, thereby forming a centering part, wherein the plurality of legs are movable between a radially expanded state and a radially restrained state.

3. The filter according to claim 2, wherein the second end of each of said at least some of the legs is joined to an intermediate portion of the leg to form a closed loop.

4. The filter according to claim 3, wherein the second end is joined to the intermediate portion at the corolla.

5. The filter according to claim 3, wherein the second end is joined to the intermediate portion at a location disposed closer to the head of the filter than to the centering pad of the leg.

6. The filter according to claim 3, wherein each of said at least some of the plurality of legs has a larger diameter section between the head and the intermediate portion where the second end is joined to the leg.

7. The filter according to claim 2, wherein the second ends of said at least some of the elongated filiform elements are joined to an outer surface of the head.

8. A blood filter adapted to be disposed in a blood vessel for retaining blood clots, the blood filter having an axis and comprising:

a head disposed substantially on the axis, and a plurality of legs extending from the head, each of at least some of the legs of the plurality of legs comprising an elongated filial element having first and second ends, with the first end being connected to an inside portion of the head and the second end being looped back and connected to an outer surface of the head to form a filial leg loop, wherein the plurality of legs are movable between a radially expanded state and a radially restrained state.

* * * * *